(12) United States Patent
Shikinami

(10) Patent No.: US 8,690,947 B2
(45) Date of Patent: Apr. 8, 2014

(54) STAND-ALONE BIOMIMETIC ARTIFICIAL INTERVERTEBRAL DISC SYSTEM

(76) Inventor: Yasuo Shikinami, Kusatsu (JP)

( * ) Notice: Subject to any disclaimer, the term of this patent is extended or adjusted under 35 U.S.C. 154(b) by 0 days.

(21) Appl. No.: 13/636,007

(22) PCT Filed: Apr. 21, 2010

(86) PCT No.: PCT/JP2010/002867
§ 371 (c)(1),
(2), (4) Date: Sep. 19, 2012

(87) PCT Pub. No.: WO2010/113530
PCT Pub. Date: Oct. 7, 2010

(65) Prior Publication Data
US 2013/0013074 A1 Jan. 10, 2013

(51) Int. Cl.
A61F 2/44 (2006.01)

(52) U.S. Cl.
USPC .................................. 623/17.16

(58) Field of Classification Search
USPC ............................ 623/17.11–17.16
See application file for complete search history.

(56) References Cited

U.S. PATENT DOCUMENTS

| | | | | |
|---|---|---|---|---|
| 3,867,728 A | * | 2/1975 | Stubstad et al. | 623/17.16 |
| 4,772,287 A | * | 9/1988 | Ray et al. | 623/17.12 |
| 5,071,437 A | * | 12/1991 | Steffee | 623/17.16 |
| 5,123,926 A | * | 6/1992 | Pisharodi | 623/17.13 |
| 5,981,619 A | * | 11/1999 | Shikinami et al. | 523/113 |
| 6,039,762 A | * | 3/2000 | McKay | 623/17.11 |
| 6,602,291 B1 | * | 8/2003 | Ray et al. | 623/17.11 |
| 6,733,531 B1 | * | 5/2004 | Trieu | 623/17.11 |
| 7,066,960 B1 | * | 6/2006 | Dickman | 623/17.16 |
| 7,731,753 B2 | * | 6/2010 | Reo et al. | 623/17.13 |
| 7,879,100 B2 | * | 2/2011 | Denoziere et al. | 623/17.11 |
| 2004/0093087 A1 | * | 5/2004 | Ferree et al. | 623/17.13 |
| 2004/0258732 A1 | | 12/2004 | Shikinami | |
| 2005/0049590 A1 | * | 3/2005 | Alleyne et al. | 606/61 |
| 2005/0273172 A1 | * | 12/2005 | Patil et al. | 623/17.16 |
| 2006/0173542 A1 | * | 8/2006 | Shikinami | 623/14.12 |
| 2007/0168031 A1 | * | 7/2007 | Hudgins et al. | 623/17.12 |

FOREIGN PATENT DOCUMENTS

| | | |
|---|---|---|
| JP | 2003-230583 A | 8/2003 |
| JP | 2009-226079 A | 10/2009 |

OTHER PUBLICATIONS

International Search Report of PCT/JP2010/002867; mailing date May 25, 2010.

* cited by examiner

Primary Examiner — Jerry Cumberledge
(74) Attorney, Agent, or Firm — Westerman, Hattori, Daniels & Adrian, LLP

(57) ABSTRACT

The artificial intervertebral disc of the present invention includes: a structured fabric having biomimetic structure and dynamic behavior, the structure comprising organic fibers, which are formed to be a cubic multi-axial three-dimensional fabric having tri-axial, to be interwoven tissues or to be a complex tissue of these; and tappets mounted on the upper surface and the lower surface of this structured fabric, wherein the tappets are connected and fitted with the connecting filaments vertically penetrating through the structured fabric. This structured fabric shows biomimetic dynamic behavior like a real intervertebral disc and achieves a clinically effective and reliable stand-alone type of biomimetic artificial intervertebral disc which can be inserted and fixed with minimally-invasive operation.

11 Claims, 5 Drawing Sheets

STAND-ALONE BIOMIMETIC ARTIFICIAL INTERVERTEBRAL DISC SYSTEM

TECHNICAL FIELD

The present invention relates to a stand-alone type of cubic multi-axial three-dimensional fabric-artificial intervertebral disc (stand-alone 3DF Disc) having a biomimetic structure, which can be inserted and fixed less-invasively, and a dynamic behavior. In further detail, the present invention relates to a clinically-truly effective and reliable stand-alone type of biomimetic artificial intervertebral disc, which has reliable fixation ability to superior and inferior vertebral bodies with preserving its biomimetic mobility and which can be easily inserted and fixed (minimally-invasive operation) into/to a space between the vertebral bodies by decreasing extension of disc space with damaging of biological vertebral bodies as much as possible and by not causing damage to the vertebral bodies as much as possible, and where the bonding state with time can also be observed at the interface with the surfaces of the vertebral bodies by X-ray images.

BACKGROUND TECHNOLOGY

The inventor of the present invention filed applications about an artificial intervertebral disc showing biomimetic mobility of intervertebral disc while binding tightly to endplates of the vertebral bodies well, in the case of inserting into a space between the vertebral bodies and receiving a biological load. One of them is an artificial intervertebral disc where a bioactive and bioresorbable solid pin(s) with high bioactivity and bio-absorbability is vertically penetrated through a structured fabric, which is a cubic multi-axial three-dimensional woven or knitted fabric of organic fibers, or, a complex structured fabric of them, and where both ends of the pin(s) are protruded from both upper and lower surfaces of the structured fabric (Patent Literature 1); and the other is an artificial intervertebral disc where the pin(s) is vertically penetrated through the inside of the structured fabric, and where the structured fabric is compressed from top and bottom sides, it is designed such that both ends of the pin are protruded from both the upper and lower surfaces of the structured fabric (Patent Literature 2). These are the stand-alone type of artificial intervertebral discs where both ends of a pin(s) protruding from both the upper and lower surfaces of a structured fabric are fitted into hole(s), which is created in endplate surfaces of the upper and lower vertebral bodies and fixed.

However, as results from insertion and mobility tests into human cadavers, and implanting tests into living baboon and other in vitro mobility tests, the following disadvantages has been recognized. In other words, when the structured fabric composed of organic fibers in as the artificial intervertebral disc is penetrated through or the inside is intruded through so as to fix the structured fabric with a pin(s) protruding from the upper and lower surfaces, it became ascertained that problems below remain. Namely, the problem described below still remain in the case that the structured fabric composed of organic fibers as the artificial intervertebral disc is fixed by the rigid pin(s), which penetrated through the fabric body or just intruded the inside protruding from top and bottom surfaces.

One problem as described below is such that insertion and fixation of the artificial intervertebral disc into/to the disc space between the vertebral bodies are difficult, and there is risk to damage the vertebral bodies or adjacent vertebral bodies due to forcible insertion.

When the artificial intervertebral disc is inserted and fixed into/to a vertebral space (disc space), which is reduced by curettage of a damaged biological intervertebral disc, first, punched holes are created in endplate surfaces contacting to the upper and lower vertebral bodies using an endplate puncher, and both ends of pins protruding from both the upper and lower surfaces of the structured fabric as an artificial intervertebral disc are fitted into these holes and a condition is reduced for inserting and fixing the artificial intervertebral disc at right positions. In order to insert the artificial intervertebral disc to the positions where the pins are set up rightly at the hole positions, because the space between the vertebral bodies has to be extended to the height including both protruding ends of the pins, it is natural that adjacent intervertebral discs located at the next superior and inferior positions should be compressed due to pressure of vertebral bodies shifted by the expanding force. In order to certainly fix the artificial intervertebral disc, the necessary length of one end of the pin protruding from the surface of the structured fabric in the artificial intervertebral disc (protruding distance) is empirically 1.0 mm to 3.0 mm, and is preferably 1.0 mm to 2.0 mm at least.

When the artificial intervertebral disc is inserted, the structured fabrics as the artificial intervertebral disc is interposed with two blades at the end portion of a catalyst as jigs. On this occasion, a dent channel with the same depth as the protruding length of the pin or a cutting channel penetrating from the top through the bottom of the blade is established in this blade to insert the artificial intervertebral disc into an intervertebral space under the ends of the protruding pin are fitted into the channels as to be adopted. However, the dent channel with the same depth as the protruding distance of the pin ends is established in the blade, which is thicker than the protruding distance of the pin end, because the thickness of the blade is greater than the protruding distance of the pin end, the intervertebral space has to be further extended to allow for the thickness of this blade. With this result, adjacent undamaged intervertebral discs located in the next disc bodies are further compressed, and risk of necrosis or damage shall be increased.

In the meantime, when the cutting channel is established in the blade with the same thickness as the protruding distance of the pin end, because the structured fabrics as the artificial intervertebral disc is grasped by blades with 1.0 mm to 2.0 (3.0) mm of thickness, which are thinner than the above-mentioned case, the expansion of the intervertebral space is controlled However, in this case, a situation where the structured fabrics of the artificial intervertebral disc is pressed and fitted so as to be along the endplate surface contour (shape) exposed in the reduced intervertebral space by the curettage cannot be obtained. In order to accelerate the bonding behavior at the interface between the endplates of the vertebral bodies and the structured fabrics as the artificial intervertebral disc, a slightly thicker structured fabric should be inserted into the intervertebral space and should be in the closely-attached state by press fitting. To that end, a method where the structured fabric is compressed from top and bottom with two blades having thickness, which is the same as the protruding distance of the pin end portion, for example, 1.0 mm to 2.0 (3.0) mm, and while the thickness of the structured fabric becomes thinner, it is inserted into the intervertebral space and set at the predetermined positions, and after the blades are removed, the structured fabric is compressed by the pressure of the upper and lower vertebral bodies and both end portions are fixed by the protruding pins shall be adopted. However, if this method is used, since the pin end portions shall protrude from the surfaces of the blades to allow for the thickness of these blades to compress the structure fabric by the blades, this is still the same situation where the intervertebral space has to be expanded by the entire length of the pins. In either case, even in the case of using the blades having a cutting channel where the top and bottom are penetrated through in order to minimize the expansion of the distance between vertebral bodies during operation, the blades must have physical strength to enable to compress the structured fabric as the artificial intervertebral disc by the thickness required for press fitting.

However, in actual, extremely great force is required to compress the structured fabric as artificial intervertebral disc even by 1.0 mm to 2.0 mm of thickness required for press fitting. For example, even in the case of the cervical spine, approximately 80 N (Newton), which is the average weight of human head, is required. Least of all, in the lumbar spine, several times higher compressive force is required than the cervical spine. In other words, the structured fabric as the artificial intervertebral disc for the cervical spine is designed to be deformed moderately with move ability responding to this compression force. In order to execute this press strength by two stainless steel blades at the end portion of the catalyst, greater than 3.5 mm thickness is required even in the case of a structured fabric as the artificial intervertebral disc for the cervical spine. If the blade is thinner than this, it warps outward and cannot compress the structured fabric evenly. Even if it is assumed to compress the structured fabric from the top and bottom by 0.5 mm each using the blades with 3.5 mm of thickness, it is necessary to expand the upper and lower vertebral bodies by at least 6.0 mm. In actuality, since it is necessary to expand the upper and lower vertebral bodies by 1.0 mm to 2.0 mm extra in order to smoothen the insertion, even in the case of insertion under compressing, 7.0 mm to 8.0 mm or greater has to be expanded. It is greatly possible to cause necrosis by compressing the adjacent intervertebral disc(s) only with keeping of such great intervertebral expansion for several minutes or longer, and it is extremely dangerous. Therefore, a method for press fitting the structured fabric to the endplate surfaces of the upper and lower vertebral bodies using such thick blades should not be clinically adopted.

As the protruding length of the pin end portions is longer (≥1.0 mm), stable stand-alone can be obtained with reliable fixation, but because of the reason above, the distance cannot be so long. Then, when it is desired to increase the protruding length of the pin at the end portions, a device to carve out a keeling channel with the same depth as the protruding length of the pin at the end portions in the endplates of the upper and lower vertebral bodies, and to penetrate the pin end portions through this channel for placing them in place can be considered. Therewith, it becomes unnecessary to expand a gap between the upper and lower vertebral bodies by the protruding length at the pin ends. This method is adopted to a currently ball and socket type of artificial intervertebral disc clinically in use, such as a two-layer structure of metal/polymer or a three-layer structure of metal/polymer/metal. However, with this method, since a healthy vertebral body is immoderately damaged only for the purpose of insertion and a combination of some adverse effects cannot be avoided, it should be avoided clinically.

Another issue is to suppress the original mobility of the structured fabric resulting from pins that penetrate through the structured fabric as the artificial intervertebral disc or that are intrude in the inside of the structured fabric.

In general, original dynamic behavior of the structured fabric upon compression or decompression is not comparatively controlled when the structured fabric is loaded heightwise (vertically), but because the constructed fiber in the X, Y and Z axes of the structured fabric is pulled by the rigid pins upon lateral bending and flexion/extension motions, the original deformation cannot be realized freely. The inventor of the present invention confirmed that the structured fabric buckles inward at the intermediate portion of the thickness of the structured fabric during the movement described above. In other words, in an experiment in vitro, observing motion pictures where these movements are simulated by interposing between artificial vertebral bodies, in the case of forward bending or backward bending, because the filament around the periphery of the structured fabric is tensioned by the pins and the structured fabric is constrained, the front surface and the rear surface of the structured fabric causes a notable buckling phenomenon inward from the intermediate portion. When this phenomenon is repeated for the long-term dynamic movement, because the fibers become overloaded, this causes deterioration or fracture of the fibers or structured fabric damage. Then, it is unavoidable to result in the destruction of the structured fabric for a long time after implanting. Similarly, a natural behavior of the structured fabric is inhibited at the time of torsional motion, as well. In other words, since the movable inhibitory effects of rigid pins causes the reduction in a ROM (range of motion) value, which is a value for rough indication of the mobility of the artificial intervertebral disc, a use of intrusion/penetration pins with such rigidity has to be avoided.

As another issue, because the pins easily move vertically within the structured fabric and the protruding distance of the pin end portions varies, the fitting of the vertebral bodies into the holes punched in the endplates is not certain, and it causes a lack of fixation reliability. Further, while they are loaded and the structured fabric is dynamically deformed, the pins themselves is bent due to their deformation force, and it is possible to extract the structured fabric from the holes punched in the endplate and to dislocate it from the disc space, thus a lack of fixation for a long term is also mentioned.

PRIOR ART DOCUMENTS

Patent Literature

[Patent Literature] Japanese Patent Application Laid-Open No. 2003-230583
[Patent Literature] WO No. 09/084,559

SUMMARY OF THE INVENTION

Problem to be Solved by the Invention

The present invention has been accomplished in order to deal with the problems above. In other words, the problem to be solved by the invention is solved by providing an artificial intervertebral disc using a cubic multi-axial three-dimensional interwoven or interknitted structured fabric, which is a clinically-truly effective and reliable stand-alone type of biomimetic artificial intervertebral disc that has reliable fixation to upper and lower vertebral bodies, and that can be easily inserted and fixed minimally into/to a space between the vertebral bodies by decreasing intervertebral expansion as much as possible and by not causing damage to the vertebral bodies as much as possible, and where the bonding state with time can also be observed at the interface with the surfaces of the vertebral bodies by X-ray images.

Means for Solving the Invention

In order to solve the problems, the stand-alone type of biomimetic artificial intervertebral disc relating to the present invention is characterized by having: the structured fabrics comprising organic fibers, which are formed to be a cubic multi-axial three-dimensional fabric structure having three axes, to be interwoven, interknitted or a complex structure of these; and tappets (also referred to as "dot pins" or "convex stoppers") mounted on the upper surface and the lower surface of this structured fabric.

In the stand-alone type of biomimetic artificial intervertebral disc of the present invention, it is preferable that the tappets mounted on the top surface of the structured fabric (upper surface-side tappets) and the tappets mounted on the lower surface (lower surface-side tappets) are connected with the connecting filaments (threads) vertically penetrating through the structured fabric under a condition of tension added. Then, when the tappets are fitted into the holes created in the endplate surfaces of the upper and lower vertebral bodies and the structured fabric as the artificial intervertebral disc is fixed in a stand-alone manner, it is preferable that the height [0015]

In the stand-alone type of biomimetic artificial intervertebral disc of the present invention, it is preferable that the tappets mounted on the top surface of the structured fabric (upper surface-side tappets) and the tappets mounted on the lower surface (lower surface-side tappets) are connected with the connecting filaments (threads) vertically penetrating through the structured fabric under a condition of tension added. Then, when the tappets are fitted into the holes created in the endplate surfaces of the upper and lower vertebral bodies and the structured fabric as the artificial intervertebral disc is fixed in a stand-alone manner, it is preferable that the height of the tappets is 1.0 mm to 3.0 mm and the contacting surface of the structured fabric to the tappet is formed on the convex surface or the concave surface that convexly deforms or concavely deforms toward the flat surface of the structured fabric side, respectively. This is because the tappets make it difficult to be sunk into by mounting onto the filaments (thread) constituting the structured fabric, and the tappets can be easily popped out of the surface due to repulsive force of the filaments (thread) constituting the structured fabric. Further, when the tappets are clung to the endplate surfaces of the vertebral bodies, which are roughened by a rasp as mentioned later, and the structured fabric as the artificial intervertebral disc is fixed in a stand-alone manner, it is preferable to mount at least five each (needless to say, the number is not limited to five) of the tappets on both upper and lower surfaces of the structured fabric. Furthermore, in both cases, the height of the top-surface side tappet and that of the bottom-surface side tappet can be the same or different.

It is preferable that the tappet is made of either radiopaque bioceramics or radiopaque and bioactive bioceramics. However, when a bonding property with the vertebral bodies is added by applying a treatment to spray powder of the bioactive bioceramics onto both the upper and lower surface layers of the structured fabric, a tappet made of a complex of radiopaque and bioactive, bioabsorbable bioceramics, and, biodegradable, bioabsorbable polymer is also preferably used.

Further, the upper and lower surface layer portions of the structured fabric are preferably more flexible than other portions of the structured fabric. Then, it is preferable that powder of the bioactive bioceramics is sprayed onto the upper surface layer and the lower surface layer of the structured fabric or the upper surface layer and the lower surface layer of the structured fabric are coated with a complex of powder of the bioactive bioceramics and the biodegradable, bioresorbable polymer. With this material, bone on the surfaces of vertebral bodies and the structured fabric is bound, and stand-alone fixation with enhanced reliability can be obtained.

Effect of the Invention

When the stand-alone type of biomimetic artificial intervertebral disc relating to the present invention is inserted and fixed into the intervertebral space, the artificial intervertebral disc is compressed from top and bottom with two blades as insertion jigs (blades without any channels), and the tappets are pressed to the upper surface and the lower surface of the structured fabric to become flush ends of the tappets, which are placed on the upper surface and the lower surface of the structured fabric, with the upper surface and the lower surface of the structured fabric, and the artificial intervertebral disc is inserted into a space, which is slightly wider clearance than the total height of the structured fabric and the two blades, between upper and lower vertebral bodies. Then, when the two blades are removed, the tappets, which are pushed and sink into the upper surface and the lower surface of the structured fabric, are restored to the original protruding state due to repulsion force of the structured fabric (elastic restoring force), and they are fitted into holes created in the endplate surfaces of the upper and lower vertebral bodies, and with this movement, the artificial intervertebral disc of the present invention is fixed in a stand-alone manner between the upper and lower vertebral bodies.

In that case, if the structured fabric as the artificial intervertebral disc of the present invention is thicker than the clearance height between the vertebral bodies (distance between vertebral bodies before widening) by 0.5 mm to 1.0 mm at one side and 1.0 mm to 2.0 at both sides, when the separated upper and lower vertebral bodies are restored to the original distance between the vertebral bodies after the artificial intervertebral disc is inserted, both the upper and lower surfaces of the structured fabric are firmly contacted under the condition to be slightly compressed along the endplate surface contour of the upper and lower vertebral bodies. Such compressed and contacted condition is preferable to obtain excellent bone bonding between the structured fabric and the vertebral bodies according to osteoconduction (osteoinduction) of the bioceramic powder when both the upper and lower surface layers of the structured fabric is treated by spraying bioactive bioceramic powder.

Since the artificial intervertebral disc of the present invention is to push and sink the tappets on both the upper and lower surfaces of the structured fabric into both the upper and lower surfaces with two blades as insertion jigs, when the artificial intervertebral disc is inserted into a space between the upper and lower vertebral bodies, no great compression force required; therefore, for the blades as the insertion jigs, thin stainless blades with approximately 0.5 mm of thickness are sufficient. Consequently, both the upper and lower vertebral bodies should be separated by 1.0 mm, which is the thickness of the two blades, and an extra gap 1.0 mm to 2.0 mm, for a total of 2.0 mm to 3.0 mm at both sides, and the upper and lower vertebral bodies should be separated by 3.0 mm to 5.0 mm at both sides even when the structured fiber, which is approximately by 1.0 mm to 2.0 mm thicker at both sides than the distance between the vertebral bodies (clearance height between the vertebral body before separating) in order to be compressed and contacted, is used. Thus, in the artificial intervertebral disc of the present invention, since an intervertebral expansion becomes substantially one-half or less compared to the conventional artificial intervertebral disc using rigid penetration pins or intrusion pins where the upper and lower vertebral bodies have to be separated by 7.0 mm to 8.0 mm at both sides, the risk to necrotize or cause damages of adjacent intervertebral discs is eliminated and it also becomes unnecessary to apply any special method to the intervertebral expansion.

In the artificial intervertebral disc of the present invention, since the tappets mounted on the upper surface of the structured fabric and the tappets mounted placed on the lower surface of the structured fabric are connected with connecting filaments that vertically penetrate through the structured fabric under a condition of tension added, the tappets will never be separated or displaced from the structured fabric but the stable mounted state can be maintained, and in addition, because the connecting filaments will never be an impediment when the tappets are pushed into the upper and lower surfaces of the structured fabric, the tappets can be easily pushed and lowered with small compression force. Then, since this connecting filament does not restrain any dynamic motion by tensioning a constituent filament of the structured fabric at the time of lateral bending movement or extension-flexion bending motion, like penetration pins or intrusion pins with rigidity in the conventional artificial intervertebral disc, defects to prevent biomimetic deformation unique to the structured fabric or to cause a buckling phenomenon inward at the intermediate portion of thickness of the structured fabric can be eliminated.

Further, in the artificial intervertebral disc where the tappets are fitted into holes created in the endplate surfaces of the upper and lower vertebral bodies and they are fixed in a stand-alone manner, the tappet height is adjusted at 1.0 mm to 3.0 mm, and an abutting surface (bottom surface) of the tappet with the structured fabric should be a flat surface, or, a convex curve or a concave curve convexly or concavely curved toward the structured fabric. If the tappet height is 1.0 mm or higher, it is preferable because the tappets are certainly fitted so as not to slip away from the holes of the endplate surfaces of the vertebral bodies, and if it is 3.0 or less, it is also preferable because it is unnecessary to make extra deep holes in the endplate surfaces of the vertebral bodies. Then, the mounting stability of the tappet whose bottom surface is formed to be flat is excellent, and in the tappets whose bottom surface is formed to be a convex curve or concave curve that is convexly or concavely curved toward the structured fabric side, respectively, an area of the bottom surface becomes greater than that of the flat surface to some extent, and more filaments constituting the structured fabric shall lay on the bottom of the tappet by the area, thus the mounting stability of the tappets is further improved. Therefore, when both the upper and lower surfaces of the structured fabric are depressed and pushed down while the tappets are compressed with the blades as the insertion jigs, there is no concern that the tappets may be displaced, and in addition, at the same time of removing the blades, since the tappets are stably and upright fitted into the holes in the endplate surfaces of the vertebral bodies due to elastic restoring force of the filaments constituting the structured fabric and the tappets will never slip away from the holes, the structured fabric can be certainly fixed so as not to dislodge the structured fabric from the intervertebral [space]. Particularly, in the case of the convex curve, even if the tappets are inserted and mounted while the tappets' positions are slightly shifted from the holes created in the endplate surfaces, because the ends of the tappets vibrate according to a curvature of the bottom surface by slightly shaking them, the tappets are easily fitted into the holes.

In the meantime, for the artificial intervertebral disc that is fixed in a stand-alone manner by hanging the tappets to the endplate surfaces of vertebral bodies roughened by a rasp, it is better to adjust the tappet height at 0.3 mm to 1.0 mm and to mount at least five each of the tappets both on the upper and lower surfaces of the structured fabric. If the tappet height is 0.3 mm or higher, it is preferable because the tappets are certainly clung to the endplate surfaces of the roughened vertebral bodies and the artificial intervertebral disc can be fixed in a stand-alone manner, and compressive contacting between the endplate surfaces and both the upper and lower surfaces of the structured fabric will never be impaired if the height is 1.0 mm or less. Further, the number of tappets to be mounted on both the upper and lower surfaces of the structured fabric is at least five each, the tappets are clung to the endplate surface of the vertebral bodies and slip resistance becomes greater, and any dislodging of the artificial intervertebral disc can be certainly prevented.

Further, in the artificial intervertebral disc of the present invention, if the tappet is made of radiopaque bioceramics, because the tappets are detected by the X-ray, whether or not the tappets are well-fitted into the holes in the endplate surfaces of the vertebral bodies can be observed through the X-ray imaging, and a position of the structured fabric immediately after the surgery or after passage of a long time and a combining state on the interface with the vertebral bodies can be observed. Then, if the tappet is made of radiopaque and bioactive bioceramics, in addition to the above, there is an advantage that the bone tissue is conductively formed on the tappets from the vertebral bodies due to the osteoconductivity of the bioactive bioceramics, and the vertebral bodies and the tappets are bound. In addition, if the tappet is made of a complex of powder of the radiopaque and bioactive, bioresorbable bioceramics and a biodegradable, bioresorbable polymer, the bone tissue is conductively formed on the tappets from the vertebral bodies due to the osteoconductivity of the bioceramic powder to be exposed in association with the progress of hydrolysis of the biodegradable, bioresorbable polymer, and both the polymer in the tappets and the bioceramic powder are absorbed at last, and the tappets are totally substituted by the bone tissue and disappear, and there is an advantage that the holes in the endplate of the vertebral bodies are filled with the totally-substituted bone tissue and repaired. In fact, when the tappets made of this complex are mounted, if a treatment to add a binding property with the vertebral bodies to both the upper and lower surface layers of the structured fabric (a treatment to spray powder of bioresorbable and bioactive bioceramics) is applied so as to bind the structured fabric with the vertebral bodies by the time when tappets disappear, even after the tappets no longer exist, a position gap or dislodging can be prevented. In this case, if the bioactive bioceramics without bio-absorbability is used, since this powder flows out to other parts and may cause a foreign body response to an unexpected tissue, powder of bioresorbable and bioactive bioceramics should be used.

Further, in the artificial intervertebral disc of the present invention, if the upper and lower surface layers of the structured fabric are more flexible than the interlayer portion of the structured fabric, this is preferable because the surfaces of the surface layer portions certainly express the compressive fitting along the contour of the endplate surfaces of the vertebral bodies after maintenance by their own weight of the upper portion after this structured fabric is mounted in the space between the vertebral bodies.

In addition, in the artificial intervertebral disc of the present invention, for one where powder of the bioactive bioceramics is sprayed onto the upper and lower surface layers of the structured fabric, the bone tissue is conductively formed both on the upper and lower surface layers of the structured fabric from the vertebral bodies due to the osteoconductivity of the bioceramic powder, and, the bone tissue intertwines with organic fibers both in the upper and lower surface layers of the structured fabric and the vertebral bodies are bound with the structured fabric, stand-alone fixation of the artificial intervertebral disc is improved and a concern about dislodging from the intervertebral space can be avoided.

Further, in the artificial intervertebral disc of the present invention, the one where in the upper and lower surface layers of the structured fabric are coated with a complex of the bioactive bioceramics and the biodegradable, bioresorbable polymer, the bone tissue is conductively (inductively) formed both on the upper and lower surface layers of the structured fabric from the vertebral bodies due to the osteoconductivity and osteoinductivity of the bioceramic powder to be exposed in association with the progress of the hydrolysis of the biodegradable, bioresorbable polymer and is substituted by the polymer, and as similar to the above, because the bone tissue intertwines with the organic fibers both in the upper and lower surface layers of the structured fabric and the vertebral bodies are bound with the structured fabric, stand-alone fixation of the artificial intervertebral disc becomes perfect and any concern about dislodging from the intervertebral space is eliminated.

MODE FOR CARRYING OUT THE INVENTION

Hereafter, a specific embodiment of the present invention is described in detail with reference to drawings.

Figure 1:
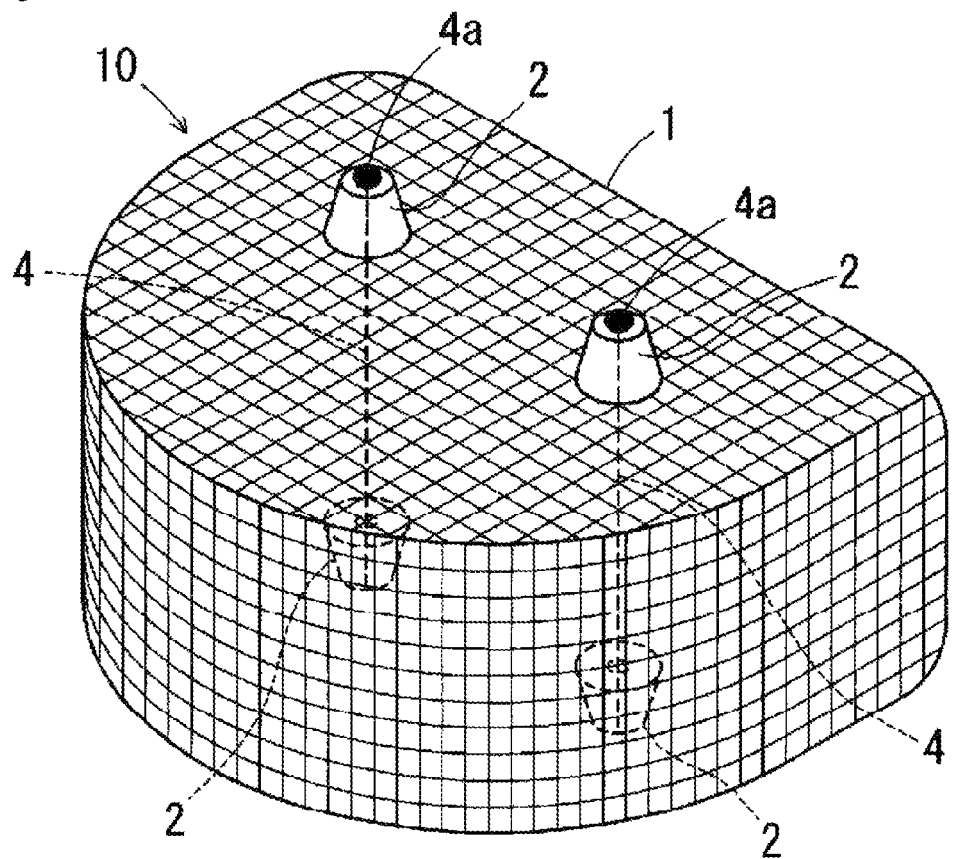
FIG. 1 is a perspective view of a stand-alone type of biomimetic artificial intervertebral disc relating to one embodiment of the present invention.
Figure 2:
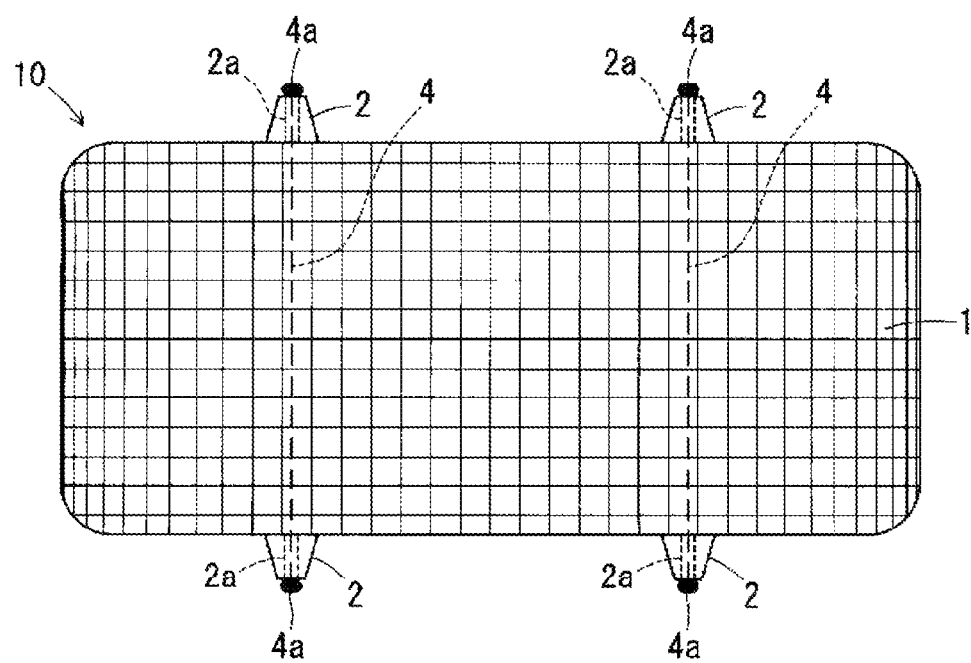
FIG. 2 is a front view of the artificial intervertebral disc.
Figure 5:
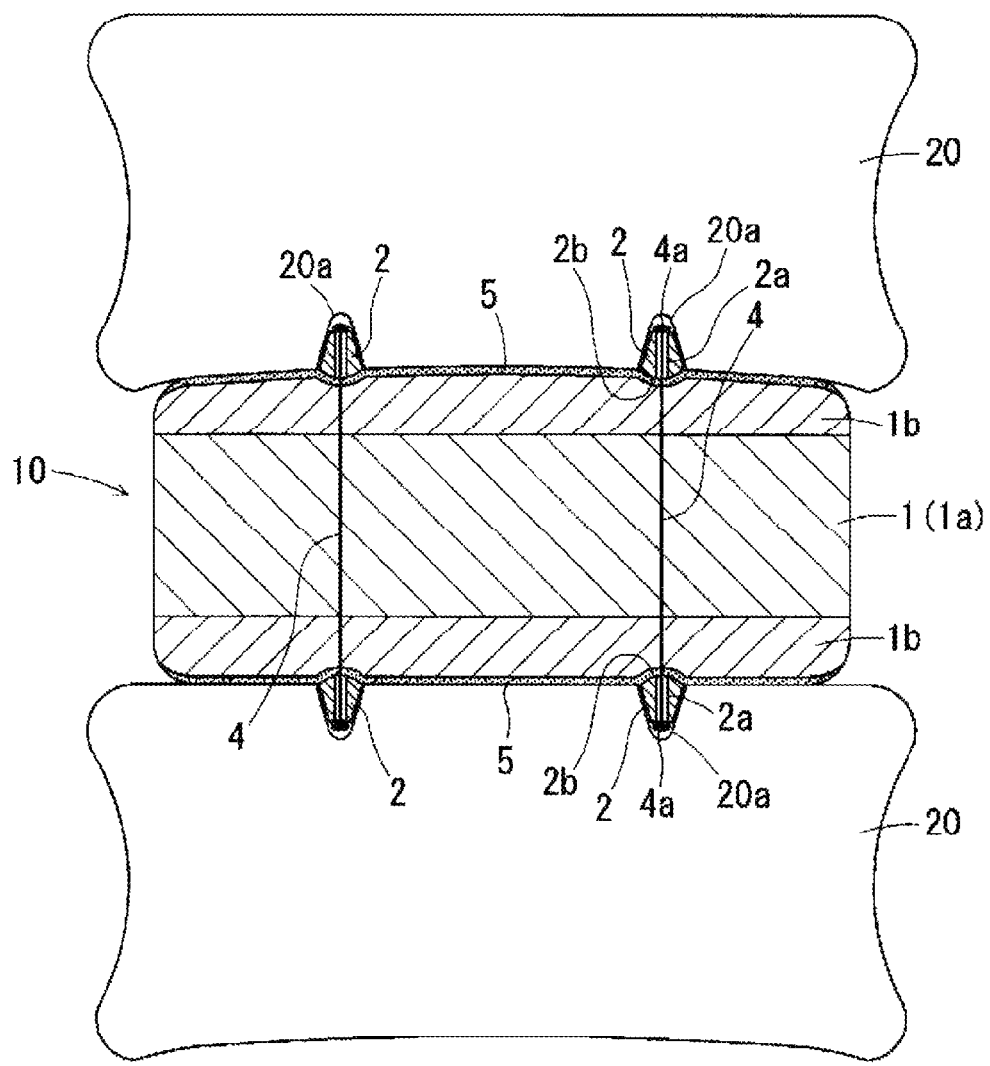
FIG. 5 is a schematic cross-sectional view of the artificial intervertebral disc placed between the upper and lower vertebral bodies.

A stand-alone type of biomimetic artificial intervertebral disc 10 shown in FIG. 1 and FIG. 2, is a total substitution type of artificial intervertebral disc to be inserted and fixed between upper and lower vertebral bodies 20 and 20 of the cervical spine, thoracic spine or lumbar spine as shown in FIG. 5, and has a configuration, which is very much similar to a biological intervertebral disc having a planar shape whose front half is a semicircle and rear half is a rectangle, and is composed of a structured fabric 1 of organic fibers formed to be bulk and tappets 2 arranged at positions facing from each other on an upper surface and a lower surface of this structured fabric 1, respectively. The size of this artificial intervertebral disc 10 varies depending upon a human body size, and the size also varies between those for adults and children, and depending upon the size for the cervical spine, thoracic spine and lumbar spine, and for example, in the case of an artificial intervertebral disc for typical adults and for the spine, normally, the horizontal width dimension is approximately 30 mm to 40 mm, the anterior-posterior dimension is approximately 25 mm to 30 mm and the thickness is approximately 10 mm to 15 mm; and in the case of an artificial intervertebral disc for adults and for the cervical spine, normally, the horizontal width dimension is approximately 14 mm to 20 mm, the anterior-posterior dimension is approximately 10 mm to 15 mm and the thickness is approximately 8 mm to 12 mm.

The structured fabric 1 of this artificial intervertebral disc 10 is a structured fabric where organic fibers are formed to be a cubic three-dimensional fabric tissue having tri-axial or more or interwoven tissue, or, a complex tissue of these, and has static mechanical strength and flexibility and its dynamic (deformation) is extremely biomimetic. This structured fabric 1 is similar to the structured fabric described in Japanese Patent Application H6-254515 (U.S. Pat. No. 3,243,679), which has already been filed by the applicant of the present application, and if the geometric configuration is indicated with the number of dimensions and the azimuth number of a fiber array is indicated with the number of axes, it is a structure composed of a multi-axis three-dimensional fabric tissue having tri-axial or more.

The so-called three-axis three-dimensional tissue is a cubic tissue of fibers in three-axial directions: longitudinal, transverse and vertical directions, and the typical configuration of the structure is a bulk-state (plate-state or block-state) with thickness as mentioned above, and a cylindrical-state and a honeycomb-state are also realizable. This tri-axial three-dimensional tissue is categorized into an orthogonal tissue, off-angle structured fabric, entangled structured fabric and cylindrical structured fabric according to a difference of structured fabric. Further, a four-axis or greater of multi-axial three-dimensional structured fabric can improve the strength with isotropy of the structure by arranging multi-axial direction, such as 4, 5, 6, 7, 9 or 11 axes. Then, with these selections, a more biomimetic structure, which is more similar to the bio-intervertebral disc, can be optionally obtained.

Figure 3:
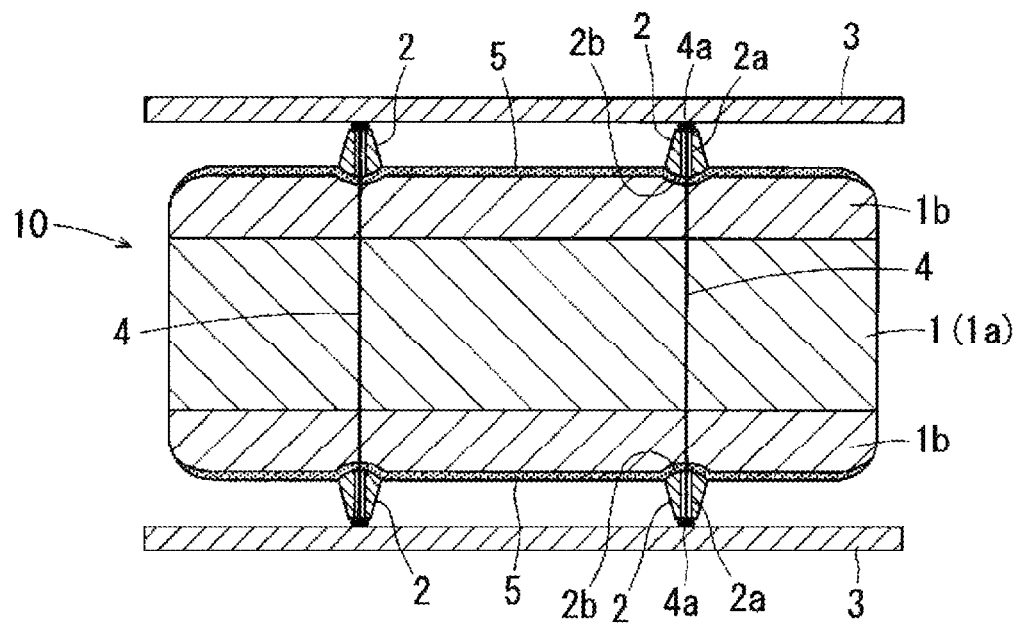
FIG. 3 is a schematic cross-sectional view of the artificial intervertebral disc, and shows a situation before the artificial intervertebral disc is compressed from top and bottom with two blades as insertion jigs.

A structured fabric 1 of this artificial intervertebral disc 10 is a production of structured fabric having various static and dynamic physical properties suitable for the intervertebral disc by devising a technology to interwoven/knitted structured fabric with the organic fibers, and as shown in FIG. 3, more flexible surface layer portions 1b and 1b than an inner layer part 1a of the structured fabric 1 are formed at both upper and lower sides interposing the inner layer 1a of the structured fabric 1. If these surface layers portions 1b and 1b are more flexible than the inner layer part 1a, when this intervertebral disc 10 is inserted into the intervertebral space, tappets 2 existing in a spot manner using blades as insertion jigs can become easily pushed into both the upper and lower surfaces of the structured fabric 1. In other words, even with a thin blade with approximately 0.5 mm of thickness, because the tappets 2 exist in a spot manner, they can be pushed into both the upper and lower surfaces of the structured fabric 1. However, even in this case, unless the tappets 2 are pinched using thick stainless blades with 3.5 mm or greater of thickness and compressed, the surface layer portions 1b and 1b cannot be entirely compressed and the thickness of the structured fabric 1 cannot be reduced. However, when a slightly thicker structured fabric (for example, one side is thicker than the distance between the vertebral bodies with approximately 0.5 mm) is selected and this is inserted, after the intervertebral space is slightly widened according to the thickness and the artificial intervertebral disc 10 is inserted and placed, when the distance between the vertebral bodies is restored to original one with a load at the upper side of the vertebral bodies, as shown in FIG. 5, because the flexible surface layer portions 1b and 1b easily follow a concave-convex contour of the endplate surfaces of the vertebral bodies 20 and 20 and are deformed to the contour, the objective to drastically improve the contact state between the structured fabric 1 and the vertebral bodies 20 and 20 can be accomplished. In other words, it is unnecessary to widen the space to a distance where double the height of the tappets 2 is added to the structured fabric 1 to be inserted, but the length of the structured fabric 1 to be inserted should be widened, and the tappets 2 at both sides are compressed with the blades with 0.5 mm of thickness and buried into both surface layers (not intruded) and the structured fabric 1 can be inserted and installed in the intervertebral space. As a method to form flexible surface layer portions 1b and 1b, for example, methods to decrease minuteness indicating the number of filaments per unit space or to reduce the filament thickness in the case when the number of filaments is the same are dominant, and the flexibility of the upper and lower surfaces layer parts 1b and 1b can be freely changed by how much the number of filaments is reduced or how much the filament thickness is decreased.

Figure 4:
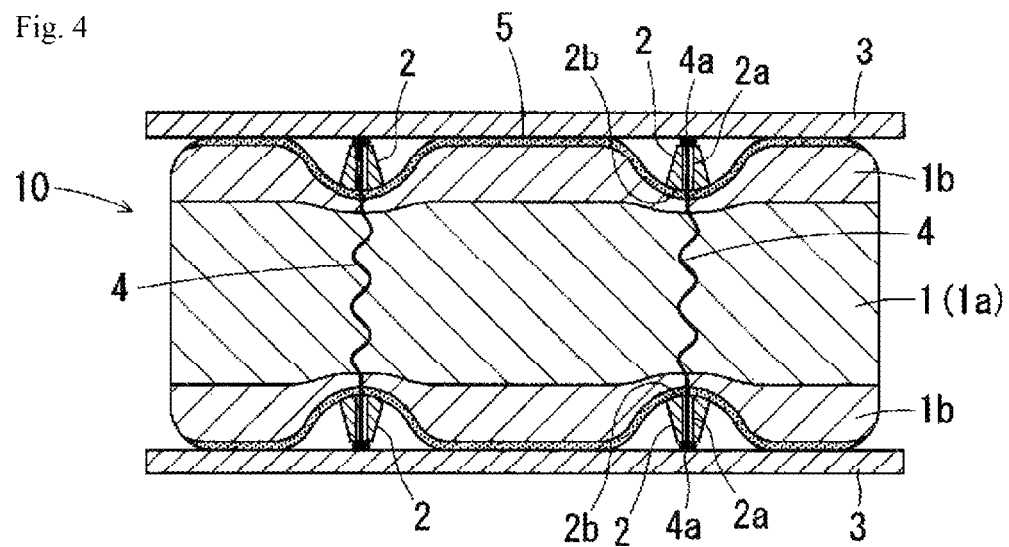
FIG. 4 is a schematic cross-sectional view of the artificial intervertebral disc, and shows a situation where the artificial intervertebral disc is compressed from top and bottom with two blades as insertion jigs.

The thickness of the flexible surface layer portions 1b and 1b is preferably greater than the height of the tappets 2, and if so, while the tappets 2 and 2 are compressed with small compression force from top and bottom with two blades 3 and 3 as insertion jigs as shown in FIG. 4, the surface layer portions 1b and 1b are depressed, and the ends of the tappets 2 and 2 can be easily pushed and buried to be flush with both the upper and lower surfaces of the structured fabric 1 (surface layer portions 1b and 1b).

In the artificial intervertebral disc 10 in this embodiment, both the upper and lower surfaces of the structured fabric 1 are flat surfaces, and the upper surface of the structured fabric 1 (surface of the upper-side surface layer portion 1b) making contact with the lower surface of the depressed endplate of the upper-side vertebral body 20 can be a raised surface that is substantially matched with the contour of the lower surface of the depressed endplate of the upper-side vertebral body 20, and in that case, since the upper-side surface layer portion 1b is substantially equally deformed by compression and tightly contacted while they are fitted into the lower surface of the upper-side vertebral body 20, there is an advantage that the pressure of the vertebral body 20 is substantially equally applied to the upper side of the structured fabric 1, and the raised upper surface also plays a role to prevent a position gap or dislodging of the structured fabric 1. Then, if they are in such contacting state, binding with the vertebral body bone is effectively accomplished. Since it is normal that the upper surface of the vertebral body 20 is flatter than the lower surface, the lower surface of the structured fabric 1 making contact with the upper surface of the lower-side vertebral body 20 can be a flat surface so as to be along the surface contour.

Furthermore, it is not an essential element that the structured fabric 1 has a three-layer structure composed of the inner layer part 1a and more flexible upper and lower surface layer portions 1b and 1b, but it can be a structured fabric with a single layer structure having appropriate flexibility.

The vacant space ratio within the structured fabric 1 is preferably within the range of 20% to 90%, and if it is 20% or greater, because the structured fabric 1 becomes minute and flexibility and a deformation property will never be impaired, it becomes a satisfactory structured fabric as the structured fabric as the artificial intervertebral disc. Further, if it is 90% or less, the dynamic and static physical properties of the structured fabric 1 are sufficient, and compression strength and shape retention will never be impaired.

As the organic fibers constituting the structured fabric 1, ones having actual performance as medical devices are selected. Bioinert synthetic resin fibers are bioinert fibers, such as polyethylene, polypropylene or polytetrafluoroethylene; and a multifilament core material for expressing flexibility using these bioinert synthetic resin fibers or anther organic fiber, and coated fibers coated with the bioinert resin to become bioinert are preferably used. Particularly, the coated fibers coated with a coating layer with linear low-density polyethylene (monofilament having, for example, 0.2 mm to 0.4 mm of diameter) as core fibers of ultrahigh molecular polyethylene are the most suitable fibers from viewpoints of strength, hardness, elasticity and easiness of weaving. Furthermore, setting aside of this, fibers having bioactivity (osteoconductivity and osteoinductivity) can be selected.

Since the structured fabric of the organic fibers is disclosed in Japanese Patent Application H6-254515 (U.S. Pat. No. 3,243,679) in detail, further explanation is omitted. Furthermore, contents of Japanese Patent Application H6-254515 (U.S. Pat. No. 3,243,679) are incorporated in this specification.

The tappets 2 mounted on the upper and lower surfaces of the structured fabric 1, as shown in FIG. 5, are to be fitted into holes 20a and 20a created in the endplate surfaces of the vertebral bodies 20 and 20 when the artificial intervertebral disc 10 is inserted into the space between the upper and lower vertebral bodies 20 and 20, and to fix the structured fabric 1 so as not to have a position gap or not to dislodge from the intervertebral space. For the reliable stand-alone fixation of the artificial intervertebral disc 10, it is necessary that the tappets 2 are mounted on both the upper and lower surfaces of the structured fabric 1 not causing to come off from the holes 20a of the endplate surfaces of the vertebral bodies 20 and to not cause the tappets 2 coming off due to horizontal bending movement or forward/backward bending movement of the structured fabric 1.

In order for the tappets 2 from slipping out of the holes 20a on the endplate surfaces of the vertebral bodies 20, it is important to set the height of the tappets 2 at 1.0 mm to 3.0 mm. If the height of the tappets 2 is 1.0 mm or higher, they will never be come off from the holes 20a on the surface of the vertebral bodies 20, and in the meantime, if the height is 3.0 mm or less, a work becomes less because the deep holes 20a do not have to be made, and, it becomes easy to work for pushing the tappets 2 down to the upper and lower surfaces of the structured fabric 1 until the ends of the tappets 2 become flush with both the upper and lower surfaces of the structured fabric 1 by the blades 3 and 3 as the insertion jigs. The further preferable height of the tappets 2 is 1.5 mm to 2.0 mm.

For the shape of the tappets 2, any effective shape to suit for various shapes of holes 20a to be created in the endplate surfaces of the vertebral bodies 20 with an endplate puncher. Since the shape of the holes 20a in the endplate surfaces of the vertebral bodies 20 is conical, the tappets 2 in the present embodiment are a beheading cone (cone whose apex is horizontally cut) to suit for the holes. For the tappets 2 with the beheading cone shape, the height is set at 1.0 mm to 3.0 mm (preferably 1.5 mm to 2.0 mm), and the diameter of the bottom surface is set at 1.5 mm to 2.0 mm and the diameter of the apex cross-section surface is set at 1.0 mm to 1.5 mm. Then, through-holes 2a with approximately 0.5 mm of the pore diameter penetrating through the connecting filaments 4 are formed on the center line of the tappets 2 in beheading cone.

The bottom surface 2b of this tappet 2, which is an abutting surface with the structured fabric 1, is formed to be a convex curve (convex sphere) convexly curved toward the structured fabric 1 as shown in FIG. 3 to FIG. 5. Consequently, the tappets 2 are stably installed in the situation where the bottom surfaces 2b of the tappets 2 slightly sink into both the upper and lower surfaces of the structured fabric 1, and as shown in FIG. 4, while the tappets 2 are compressed with the blades 3 and 3 as the insertion jigs and the upper and lower surfaces (surfaces of upper and lower surface layer portions 1b and 1b) are depressed, the tappets 2 can be efficiently pushed in, and there is less concern that the tappets 2 may be displaced, and when the blades are removed, as shown in FIG. 5, the tappets 2 stably protrude in standing posture due to elastic restoring force of filaments constituting the structured fabric on the surface layer portions 1b and 1b of the structured fabric 1, and they are fitted into the holes 20a in the endplate surfaces of the vertebral bodies 20 and 20, and a self-fixation function can be certainly demonstrated. Further, the bottom surface 2b of the tappet 2 can be a convex surface (convex sphere) or a flat surface, and even in that case, the mounting stability is excellent, and the stand-alone fixation function can be certainly exhibited.

The shape of the tappet 2 is not limited to the beheading cone, but various shapes, such as sphere, semi-sphere, spindle, beheading pyramid, cylinder or square column, are acceptable, to suit the shape of the hole 20a created in the endplate surface of the vertebral body 20. Then, the size may be changed based upon the size of the beheading cone tappet 2 to some degree.

In this artificial intervertebral disc 10, in order to mount the tappets 2 on both the upper and lower surfaces of the structured fabric 1 in order to avoid detachment of the tappets 2, the tappets 2 and 2 on both the upper and lower surfaces of the structured fabric 1 are connected with organic connecting filaments 4 vertically penetrating through the structured fabric 1 under the condition of tension added. In other words, the organic connecting filaments 4 are vertically penetrated through in between the constructing filaments of the structured fabric, and both ends of this connecting filament 4 are penetrated through the through-holes 2a of the tappets 2 and 2 on both the upper and lower surfaces of the structured fabric 1, and retaining parts 4a are formed at both ends of the connecting filaments 4 protruding from the through-holes 2a, and then, the tappets 2 and 2 on both the upper and lower surfaces of the structured fabric 1 are connected and mounted on both the upper and lower surfaces so as not to be detached. Then, when the thickness of the structured fabric 1 is restored to the original one due to release of compression by connecting the tappets 2 and 2 with the organic connecting filaments 4 under the condition of slightly compressing the structured fabric 1 from top and bottom for reducing the thickness, it is designed to add tension between the tappets 2 and 2, and the tappets 2 and 2 slightly sink and are firmly mounted in an upright posture without displacement while being mounted on both the upper and lower surfaces of the structured fabric 1.

As the organic connecting filament 4, the same one as the constituent filament made of synthetic resin fibers or coating fibers with approximately 0.2 mm to 0.4 mm of diameter used for the structured fabric 1 can be preferably used. Using the same filament is advantageous for the purpose of gain an authorized approval of the artificial intervertebral disc of the present invention. Then, the retaining part 4a of this connecting filament 4 is preferably formed with a means to make a lump having greater diameter than that of the through-hole 2a of the tappet 2 by heating and melting both ends of the connecting filament 4 with an ultrasound heater, a soldering tip or a flame burner. Furthermore, this retaining part 4a may be formed by a means to tie knots at both ends of the organic connecting filament 4. Further, the connecting filament 4 is not limited to one, but the tappets 2 and 2 on both the upper and lower surfaces of the structured fabric 1 can be connected with a plurality of connecting filaments 4.

Thus, if the tappets 2 on the upper surface of the structured fabric 1 and the tappets 2 on the lower surface 2 are connected under the condition where tension is added, because the top and bottom tappets 2 are cohered and fixed by the upper and lower surfaces under the condition where they are pulled against each other in association with the deformation of the structured fabric, it prevents the tappets 2 from detachment or displacement from the structured fabric 1 and a stable mounted state can be maintained, and in addition, since the connecting filaments 4 loosen and will never be an obstacle when the tappets 2 and 2 are pushed into the upper and lower surfaces of the structured fabric 1 with the blades 3 and 3 as the insertion jigs, respectively, the tappets 2 and 2 can be easily pushed and sunken with small compression force. Then, since this connecting filament 4 does not cause a constraint by pulling the constituent filament of the structured fabric 1 as similar to rod-state penetration pins or intrusion pins having rigidity used in the conventional artificial intervertebral disc at the time of the lateral or extension/flexion bending motion, defects to prevent a biomimetic deformation that is original to the structured fabric 1 or to cause a buckling phenomenon inward in the intermediate portion of thickness in the structured fabric 1 are eliminated.

For a material of the tappet 2, either a radiopaque bioceramics already having clinical operation or a radiopaque and bioactive bioceramics can be selected. If the tappet 2 is made of the radiopaque bioceramics, because the tappets 2 will be shown in the X-ray images, whether or not the tappets 2 are well-fitted into the holes 20a in the endplate surfaces can be observed according to the X-ray image and the position of the structured fabric 1 immediately after the operation or after long-term follow-up and a bound state in the interface with the vertebral body 20, the artificial intervertebral disc, which is truly clinically effective and have high reliability, can be obtained. Then, if the tappet 2 is made of the radiopaque and bioactive bioceramics, in addition to the above, there are advantages that a bone tissue is conductively formed in the tappet 2 from the vertebral body 20 due to the osteoconductivity of the bioactive bioceramics and the vertebral body 20 and the tappet 2 are bound.

Further, as described later, when a bonding property with the vertebral body is added to the structured fabric 1 by applying a treatment, such as spraying powder of the bioactive bioceramics both onto the upper and lower surface layers of the structured fabric 1, as the tappet 2, a complex of powder of a radiopaque bioactive bioabsorbable bioceramics and a biodegradable bioabsorbable polymer can be preferably used. If the tappet 2 is made of such complex, because the bone tissue is conductively formed in the tappets 2 from the vertebral bodies 20 due to the osteoconductivity of the bioceramic powder to be exposed in association with the progress of the hydrolysis of biodegradable bioabsorbable polymer and both a polymer of the tappets 2 and the bioceramic powder are also absorbed and the tappets are totally substituted by the bone tissue and they disappear, there is an advantage where the holes 20a created in the endplate surface of the vertebral bodies 20 are buried with the totally-substituted bone tissue and restored. Thus, even if the tappets 2 disappeared, because the structured fabric 1 is bound with the vertebral bodies 20, and a position gap and dislodging in the intervertebral space can be prevented.

As the radiopaque bioceramics to be a material of the tappet 2, an alloy of alumina, zirconia or yttrium-zirconia (YTZ) with lesser artifact compared to metal is used.

Then, as the radiopaque and bioactive bioceramics, calcined or partially-calcined hydroxyapatite, di-calcium phosphate, tri-calcium phosphate, tetra-calcium phosphate, octa-calcium phosphate, calcite, ceravital and diopcite are used, and among them, calcined or partially-calcined hydroxyapatite or β-tri-calcium phosphate having excellent osteoconductivity are preferably used.

Further, as the complex to be a material of the tappet 2, powder of radiopaque and bioactive bioabsorbable bioceramics, for example, uncalcined hydroxyapatite, calcined or partially-calcined di-calcium phosphate, tri-calcium phosphate, tetra-calcium phosphate, octa-calcium phosphate, calcite, ceravital or diopcite and crystalline poly-L-lactic acid or other lactic acid-series of biodegradable bioabsorbable polymer is used. Molecular weight of the biodegradable bioabsorbable polymer is not particularly limited, but one with approximately 100,000 to 600,000 of viscosity average molecular weight is appropriate, and according to circumstances, one whose strength is enhanced by orientating polymer particles or crystal due to forging or stretching can also be used.

It is appropriate that the content of the biodegradable bioabsorbable bioceramic powder in the complex is within the range of 20% to 50% by weight. If the content is 20% by weight or greater, the tappets 2 become clearly shown in the X-ray imaging, and because the tappets 2 are promptly decomposed and absorbed, it does not take a long time to substitute the bone tissue. In the meantime, if the content is 90% by weight or less, there is no concern to weaken the tappets 2. The further preferable content of the bioceramic powder is within the range of 25% to 50% by weight.

The number of the tappets 2 to be mounted is not particularly limited, but it is appropriate that two are mounted on the upper and lower surfaces, respectively, in the case of the artificial intervertebral disc for cervical spine in general, and three are mounted on the upper and lower surfaces, respectively, in the case of the artificial intervertebral disc for thoracic spine or lumbar spine, which is bigger than the cervical spine. However, it is normal that these are mounted at the same positions on both the upper and lower surfaces, respectively. When two of the tappets 2 are mounted on both the upper and lower surfaces of the structured fabric 1, respectively, as shown in FIG. 1 and FIG. 2, the tappets 2 can be mounted horizontally or vertically. Further, three tappets 2 are mounted on the upper and lower surfaces of the structured fabric 1, respectively, it is more appropriate to mount them at each apex of a symmetrical isosceles triangle.

It is desirable to provide a bonding property with the vertebral bodies 20 with a treatment to spray powder of radiopaque, and, bioactive bioceramics onto the upper and lower surface layers (portions to 0.5 mm to 1.5 mm from the upper and lower surfaces) of the structured fabric 1 or to coat the upper and lower surfaces layer with a complex of the bioceramic powder and the biodegradable bioabsorbable polymer, and particularly if the tappets 2 are totally substituted by the bone tissue and disappear, the reliability of self-fixation is enhanced with the treatment. Further, the symbol 5 in FIGS. 3 to 5 represents a spayed layer with the bioceramic powder or a coated layer with the complex.

If the bioactive bioceramic powder is sprayed onto the upper and lower surface layers of the structured fabric 1, because a bone tissue is conductively formed both in the upper and lower surface layers of the structured fabric 1 from the vertebral bodies due to the osteoconductivity of the bioceramic powder and the bone tissue intertwines with the organic fibers of the surface layers both in the upper and lower surfaces of the structured fabric 1, the stand-alone fixation of the artificial intervertebral disc 10 becomes perfect and any concern about dislodgement of the structured fabric 1 from the intervertebral space 1 is eliminated.

Further, if both the upper and lower surface layers of the structured fabric 1 are coated with the complex of the bioactive bioceramic powder and the biodegradable bioabsorbable polymer, because the bone tissue is conducted (inducted) and formed in both the upper and lower surface layers of the structured fabric 1 from the vertebral bodies 20 and 20 due to the osteoconductivity of the bioceramic powder to be exposed in association with the progress of the hydrolysis of the biodegradable bioabsorbable polymer and is substituted by the polymer and the bone tissue intertwines with the organic fibers in both the upper and lower surface layers of the structured fabric 1 and the vertebral bodies 20 and 20 and the structured fabric 1 is bound, the reliability of the stand-alone fixation of the artificial intervertebral disc 10 is enhanced and any concern about dislodgement of the structured fabric 1 from the intervertebral space 1 is eliminated.

Then, even in the case of the treatment to spray the bioceramic powder or to coat the surfaces with the complex, because both the upper and lower surface layers of the structured fabric 1 are shown on the occasion of X-ray imaging by the radiopaque bioceramic powder existing in both the upper and lower surface layers of the structured fabric 1, a contact condition and a binding condition between the vertebral bodies 20 and 20 and the upper and lower surfaces of the structured fabric 1 can be excellently observed.

For the bioactive bioceramic powder used for the spraying treatment, the bioabsorbable bioceramic powder to be totally substituted by the bone tissue is preferable, and considering the spraying easiness and the absorbability into a living body, ones with 30 μm or less of particle size, preferably with 10 μm or less, and more preferably with approximately 0.1 μm to 5 μm (mean grain shape: 3 μm to 5 μm) are used. Particularly, since the one having approximately 0.1 μm to 5 μm of particle size has excellent absorbability to a living body, it is preferably used.

The treatment to spray the bioceramic powder is conducted, for example, with the method mentioned below. The structured fabric 1 is placed in an airtight box, which is heated to 70° C. to 100° C.; concurrently, the bioceramic powder is placed on a metal net having finer mesh than the bioceramic powder, and it is placed under the structured fabric 1. Then, at the point when the structured fabric 1 and the bioceramic powder are heated, if air heated to 100° C. to 130° C. is spayed using a drier, the bioceramic powder sticks to the surface layers of the structured fabric 1, and is adhered not to come off. This operation is repeated several times if necessary, and an amount of the bioceramic powder to be adhered is adjusted. Furthermore, the bioceramic powder merely adhered without sticking to the surface layers gets into the surface layers by washing with ethanol or water, and a surface treatment not easily coming off is completed.

The amount of the bioceramic powder to be adhered by the spray treatment is not particularly limited, but 0.2 mg to 3 mg per unit surface area (1 cm$^2$) is preferable. If it is 0.2 mg or greater, the osteoconductive formation of the bone tissue to both the upper and lower surface layers of the structured fabric 1 is moderately faster, and the structured fabric 1 becomes easily bound with the upper and lower vertebral bodies 20 and 20 in an early stage. In the meantime, if it is 3 mg or less, the bioceramic powder that merely adheres without sticking to both the upper and lower surfaces is not increased and it becomes difficult to come off. The more preferable range is 0.5 mg to 1 mg.

As the complex to be used in the coating treatment, a complex of the bioactive bioabsorbable bioceramic powder, which is the same as that used for the spraying treatment, and a biodegradable bioabsorbable polymer, such as a copolymer of poly-D, L-lactic acid, L-lactic acid and D, L-lactic acid, a copolymer of lactic acid and glycolic acid, a copolymer of lactic acid and p-dioxanone, a copolymer of lactic acid and ethylene glycol, or a copolymer of lactic acid and polycaprolactone, whose degradation rate is comparatively high, and that has elasticity and is not fragile, and that is amorphous or is a mixture of crystal and amorphous phases, is preferable. The molecular weight of the polymers is not particularly limited, but considering the strength of the coating film or speed of degradation and absorption, ones having approximately 30,000 to 100,000 of viscosity average molecular weight are preferably used. If the viscosity average molecular weight is 30,000 or greater, it is preferable because it becomes difficult to disconnect the coating film from the organic fibers in both the upper and lower surface layers of the structured fabric 1 due to pressure or movement of the vertebral bodies 20; in the meantime, if the viscosity average molecular weight is 100,000 or less, it is preferable because it is the period of degradation and absorption becomes not to long and the conductive formation of the bone tissue to both the upper and lower surface layers of the structured fabric 1 becomes appropriately faster, and the binding between the structured fabric 1 and the vertebral bodies 20 and 20 occurs fast. For the more preferable viscosity average molecular weight of the biodegradable bioabsorbable polymers, 30,000 to 50,000 should be selected in general.

The content of the bioceramic powder in the complex for coating is preferably 50% to 95% by weight, and if the bioceramic powder is contained within this range, the bone tissue is conductively formed in both the upper and lower surface layers of the structured fabric 1 due to the osteoconductivity of the bioceramic powder, and the structured fabric 1 is bound with the vertebral bodies 20 sooner and fixed. If the content is 50% by weight or greater, the conductive (inductive) formation of the bone tissue becomes appropriately fast, and if the content is 95% by weight or less, it is preferable because it becomes difficult to weaken the coating film and there is no possibility where excess bioceramic powder may come off. The further preferable content of the bioceramic powder is 60% to 80% by weight.

Furthermore, for the bioceramic powder or the complex for spraying or coating, an appropriate amount of cytokine or drug (EP4), which are various factors for bone formation, growth and induction having osteoinductivity, bone morphogenetic protein (BMP), platelet-rich-plasma (PRP) or bone mallow cell (BMC) can be contained, and in that case, the bone induction becomes remarkable, and the growth and substitution of the bone tissue in both the upper and lower surface layers of the structured fabric 1 are remarkably accelerated, and it is advantageous because the structured fabric 1 is bound with the vertebral bodies 20 sooner. Similarly, an appropriate amount of the above-mentioned ones can be contained in the tappets 2 made of a complex composed of the bioceramic powder and the biodegradable bioabsorbable polymer.

The coating treatment is conducted as follows: the biodegradable bioabsorbable polymer is dissolved into a volatile solvent, such as ethanol, dichloroethane (methane) or chloroform; concurrently, the content of the bioceramic powder is uniformly mixed for preparation of a suspension, and both the upper and lower surfaces of the structured fabric 1 are coated with this suspension, or, this suspension is sprayed onto both the upper and lower surfaces of the structured fabric 1, or, both the upper and lower surfaces of the structured fabric 1 are immersed into this suspension liquid. In that case, a wetting characteristic is improved by applying corona discharge, a plasma treatment or an oxide treatment, such as a hydrogen peroxide treatment, in advance, and this makes migration and growth of bone tissue effective.

The thickness to coat both the upper and lower surfaces layer of the structured fabric 1 with the complex (thickness to penetrate the complex from both the upper and lower surfaces) is preferably up to 0.5 mm to 1.5 mm of depth from the upper and lower surfaces, and the bone tissue and the vertebral bodies 20 and 20 are strongly bound with this degree of thickness, and in addition, it prevents the bone tissue from migrating into the inner layer portion 1a of the structured fabric 1, and the structured fabric 1 plays a similar role to a living intervertebral disc (biomimetic) and is deformed, and sufficiently plays a role as an artificial intervertebral disc. If the thickness to coat the surface layers is 0.5 mm or greater, the bone tissue layer to be conductively (inductively) formed will not become too thin, and the intertwining between the organic fibers in both the upper and lower surfaces and the bone tissue becomes sufficient and the bounding strength between the structured fabric 1 and the vertebral bodies 20 can be secured. In the meantime, the thickness to coat the surface layers is 1.5 mm or less, the thickness of the inner layer portion of the bioinert structured fabric 1 body where no bone tissue is conductively formed will not be relatively too thin, and the structured fabric 1 is sufficiently deformed to become biomimetic, and a function as an artificial intervertebral disc can be secured. The further preferable thickness to coat the surface layers with the complex is 0.7 mm to 1.0 mm. Furthermore, the thickness to coat the surface layers with the complex can be easily adjusted by adjusting the viscosity of the coating suspension or by adjusting a coating amount.

When the spraying treatment with the bioactive bioceramic powder or the coating treatment with the complex is applied onto both the upper and lower surface layers of the structured fabric 1, and, what will be totally substituted by the bone tissue and disappear are installed in both surfaces of the structured fabric 1 as the tappets 2 and connected with the connecting filaments 4, a connecting filament made of a biodegradable bioabsorbable polymer, such as poly-lactic acid, poly-glycol acid, a copolymer of lactic acid and glycol acid, or polydioxanone, which is degraded and absorbed in vivo after the structured fabric 1 and the upper and lower vertebral bodies 20 and 20, may be used as the connecting filament 4. Even if such connecting filament 4 is degraded and absorbed and the tappets 2 disappear, since the structured fabric 1 is bound with the upper and lower vertebral bodies 20 and 20, there is no concern about a position gap or dislodging of the structured fabric 1, and the structured fabric 1 singularly plays a role as an intervertebral disc. Further, there is an advantage where the connecting filaments 4 and the tappets 2 do not remain in vivo as foreign bodies. Since the connecting filament of polydioxanone has a stretching property, it is effective when stretching of the intervertebral space in the compression direction is considered.

Next, an operation method where the artificial intervertebral disc 10 of the present embodiment is inserted between the upper and lower vertebral bodies 20 and 20, and is set by compressive contact is explained.

First, an intervertebral disc, which has been damaged to be irreparable with other medical treatments, is curetted away and the intervertebral space is reduced, and the holes 20a and 20a are created in the endplates of the upper and lower vertebral bodies 20 and 20 with a puncher. Then, the artificial intervertebral disc 10 where the thickness of the structured fabric 1 is slightly thicker than the distance between the upper and lower vertebral bodies (distance before expanding the intervertebral space), preferably at approximately 0.5 mm at one side or at approximately 1.0 mm at both sides, is selected, as shown in FIG. 3, and this artificial intervertebral disc 10 is pitched with two stainless blades 3 and 3 with 0.5 mm of thickness as tool jigs and is compressed from the top and bottom as shown in FIG. 4. Then, the tappets 2 and 2 mounted on both the upper and lower surfaces of the structured fabric 1, as shown in FIG. 4, are pushed in an upright posture while the top and bottom flexible surface layer portions 1b and 1b, which are mounted on the filaments constituting the structured fabric 1, are depressed, and the connecting filaments 4 are loosened by the pushed distance of the tappets 2 and 2, and the tappets 2 and 2 shall sink to the depth where the ends of the tappets 2 and 2 and both the upper and lower surfaces of the structured fabric 1 become flush. In that case, since the tappets 2 and 2 are connected with the connecting filaments 4, they will never be displaced, but sink in vertically to the surfaces, respectively. Further, since what are directly compressed by the blades 3 and 3 are only the tappets 2 and 2, which are scattered in a spot manner, and the entire surface of the structured fabric 1 is not compressed, this pushing operation can be easily performed with the thin stainless blades 3 and 3 with approximately 0.5 mm of thickness. The reason why extremely great compression force is required when the entire surface of the structured fabric 1 is pushed and compressed is because the filaments in the X, Y and Z-axes interwoven to be cubic three-axial three-dimensional are pulled against each other upon compression and deformed, and they function as prohibitive force for the deformation. This appears when the entire surface is compressed, and when the tappets scattered in a spot manner are pushed, because the effect is not the entire preventive movement of the filaments from each other, but is the deformation of the filaments in a spot manner under the tappets 2, the tappets 2 are deformed merely by applying a small weight, and the tappets 2 can sink in from the surface.

For example, when the structured fabric 1, which is thicker than the actual interval of the intervertebral space after restoration by 0.5 mm at one side or by 1.0 mm at both sides is pinched from top and bottom with the blades 3 and 3 with 0.5 mm of thickness and is inserted into the intervertebral space in consideration to tightly contact along the surface contour of the vertebral bodies 20, it is necessary to theoretically widen the intervertebral space by 2.0 mm from the actual intervertebral space. In actuality, since it is easier to operate by widening approximately 0.5 mm to 1.0 mm extra so as to make it easy for insertion, it is necessary to expand 2.5 mm to 3.0 mm at most, but since any abnormal compression will never be transmitted to adjacent intervertebral discs, no adjacent intervertebral disc will become necrotic during the surgery. Thus, if the artificial intervertebral disc of the present invention is used, because excessive expansion of an intervertebral space can be reduced, the surgical operation upon insertion is performed less invasively and the risk of necrosis or damage because of compression of adjacent intervertebral disc is eliminated, and it also becomes unnecessary to adopt any special expansion tools or methods for the intervertebral expansion. In the meantime, in order to entirely push the upper and lower surfaces of the structured fabric 1 as described above, since 3.5 mm or greater of thickness is required in the blades empirically, 8.0 mm or greater of intervertebral expansion becomes required even if there is 1.0 mm of interval at both sides upon the insertion, the risk of causing the adjacent intervertebral disc to become necrotic or damaged becomes extremely high.

As described above, the artificial intervertebral disc 10 is compressed with the two blades 3 and 3 as insertion jigs and is inserted into slightly expanded intervertebral space, and while the structured fabric 1 of the artificial intervertebral disc 10 is pushed with stoppers of the insertion jigs so as not to be regressed, if the two blades 3 and 3 are removed from the intervertebral space, the upper and lower surfaces layer portions 1b and 1b of the structured fabric 1 are expanded and restored to be the original state due to elastic restoring force of filaments, and the tappets 2 and 2 are ejected as in the upright state from the depression of the surface layer portions 1b and 1b and are restored to the protruding state from the upper and lower surfaces of the structured fabric 1, and the ends of the tappets 2 and 2 are fitted into the holes 20a and 20a in the endplate surfaces of the upper and lower vertebral bodies 20 and 20. Then, when the load of the head portion above the vertebral bodies is added and the intervertebral space is compressed and the original distance between the vertebral bodies is restored, as shown in FIG. 5, the upper and lower surfaces layer portions 1b and 1b of the structured fabric 1 are compressed by the vertebral bodies 20 and 20 by approximately 0.5 mm, respectively, and are compressed and cohered along the surface contour of the endplates of the vertebral bodies 20 and 20; concurrently, the tappets 2 and 2 in both the upper and lower surfaces are completely fitted into the holes 20a and 20a in the endplate surfaces, and this causes the stand-alone fixation of the artificial intervertebral disc 10 in the intervertebral space, and any concern about the position gap or dislodging is eliminated. Further, in order to facilitate the removal of the blades 3 and 3, it is desirable to apply a fluorine treatment to the surfaces of the blades 3 and 3 to be slippery.

Thus, when the artificial intervertebral disc of the present invention is inserted and placed in the intervertebral space, the structured fabric functions to be biomimetic behavior, which is very similar to the biological intervertebral disc, and sufficiently plays a role of the intervertebral disc. In other words, this artificial intervertebral disc has a structure where the tappets 2 and 2 on both the upper and lower surfaces of the structured fabric 1 are connected with the connecting filaments 4 penetrating through the structured fabric in the vertical direction, and since the connecting filaments 4 never constrain the constituent filaments of the structured fabric by pulling upon lateral bending or extension/flexion bending motion, any concern to prevent the biomimetic deformation that is original to the structured fabric 1 or to cause a buckling phenomenon inward in the center portion of the thickness of the structured fabric 1 can be eliminated.

Further, in this artificial intervertebral disc 10, the tappet 2 is made of a radiopaque material, such as radiopaque bioceramics, and because the radiopaque bioactive bioceramic powder is sprayed onto both the upper and lower surface layers of the structured fabric 1 or both the upper and lower surface layers of the structured fabric 1 is coated with a complex of the powder and a biodegradable bioabsorbable polymer, when the intervertebral space where this artificial intervertebral disc 10 is inserted and placed and is X-ray imaged and the tappets 2 and 2 and both the upper and lower surface layers of the structured fabric 1 are projected from sides, whether or not the tappets 2 and 2 are well-fitted into the holes 20a and 20a of the endplate surface of the vertebral bodies 20 and 20, respectively, or, the position of the structured fabric 1 or a contact state or binding state between both the upper and lower surfaces of the structured fabric and the vertebral bodies 20 and 20 can be observed, and in addition, both the upper and lower surfaces of the structured fabric 1 and the upper and lower vertebral bodies 20 and 20 maintain their binding state over time as described above and the structured fabric 1 is completely fixed in a stand-alone manner; therefore, the artificial intervertebral disc 10 is truly clinically effective and will acquire high reliability.

In the artificial intervertebral disc 10 of the embodiment, the tappets 2 and 2 on the upper and lower surfaces of the structured fabric 1 are mounted so as not to be displaced by connecting with the connecting filaments 4 with slight tension added, but the tappets 2 and 2 can be mounted to both the upper and lower surfaces of the structured fabric 1 so as not to be displaced with another means, for example, a means to directly sew the tappets 2 to the upper and lower surfaces of the structured fabric 1 with suitable filaments.

The artificial intervertebral disc 10 is a type where the tappets 2 and 2 are fitted into the holes 20a and 20a created in the endplate surfaces of the upper and lower vertebral bodies 20 and 20 and the structured fabric 1 is fixed in a stand-alone manner, and if this is an artificial intervertebral disc, which is a type where the tappets 2 and 2 are clung to the endplate surfaces of the vertebral bodies 20 and 20 roughened with a rasp and the structured fabric 1 is fixed in the stand-alone manner, at least five comparative small tappets 2 and 2 should be mounted in both the upper and lower surfaces of the structured fabric 1, respectively, and, the height of the tappet 2 should be 0.3 mm to 1.0 mm, preferably approximately 0.5 mm. If the tappet height is 0.3 mm or greater, the tappets 2 and 2 are certainly clung to the endplate surface of the roughened vertebral bodies 20 and 20 and the structured fabric 1 is certainly fixed in the stand-alone manner; in the meantime, if the tappet height is 1.0 mm or less, there is an advantage where there is no longer the concern about the impairment of the tightly contact by compression between the endplate surfaces and both the upper and lower surfaces of the structured fabric 1. Further, the number of the tappets 2 and 2 to be installed on both the upper and lower surfaces of the structured fabric 1 is at least five, respectively, the tappets 2 and 2 are clung to the endplate surfaces of the vertebral bodies 20 and 20 and slip resistance becomes greater and it becomes possible to certainly prevent the artificial intervertebral disc from dislodging. The upper limit of the number of the tappets 2 and 2 to be mounted on both the upper and lower surfaces of the structured fabric 1, respectively, varies according to the size of the tappet 2 or the size of the structured fabric 1, and it is appropriate to set up to 30 tappets, respectively. Furthermore, the diameter of the end surface and the bottom surface of the tappet 2 in this case is set within the range of 0.6 mm to 1.0 mm by considering the diameter of the through-hole 2a and thickness of the connecting filament 4, and it is preferable to set the diameter of the hollow through-hole 2a within the range of 0.3 mm to 0.5 mm according to the thickness of the connecting filament 4.

Figure 6:
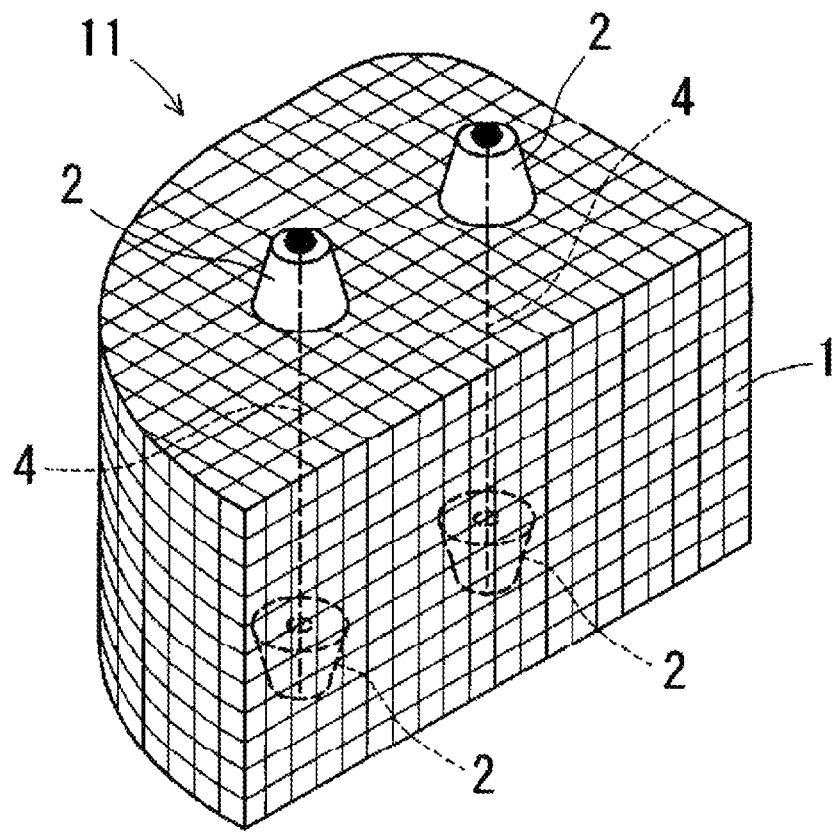
FIG. 6 is a perspective view of the stand-alone type of biomimetic artificial intervertebral disc relating to another embodiment of the present invention.

Next, with reference to FIG. 6, the stand-alone type of biomimetic artificial intervertebral disc relating to another embodiment of the present invention is further explained.

This artificial intervertebral disc 11 is a partially-substitution type of artificial intervertebral disc where one-half of the intervertebral disc is substituted, and it has a laterally-halved shape of the totally-substitution type of artificial intervertebral disc 10. The configuration of this artificial intervertebral disc 11 is substantially the same as that of the artificial intervertebral disc 10, and two tappets 2 are mounted vertically on both the upper and lower surfaces of the structured fabric 1 with organic fibers where flexible top and bottom surface layer portions are formed, respectively; and the tappets 2 and 2 on the upper and lower surfaces are connected with the connecting filaments 4 vertically penetrating the structured fabric 1 under a condition with tension added; concurrently, bioactive bioceramic powder is sprayed onto both the upper and lower surfaces of the structured fabric 1 or both the upper and lower surfaces of the structured fabric 1 is coated with a complex of the ceramic powder and a biodegradable bioabsorbable polymer, and a bonding property with the vertebral bodies is provided.

Since such partially-substitution type of artificial intervertebral disc 11 can be inserted into one side between the vertebral bodies from the backside, compared to the one to be inserted into the space between the vertebral bodies from the front side like the totally-substitution type of artificial intervertebral disc 11, a surgery can be easily performed. Then, this artificial intervertebral disc 11 also demonstrates a superior function effect as similar to the artificial intervertebral disc 10.

Figure 7:
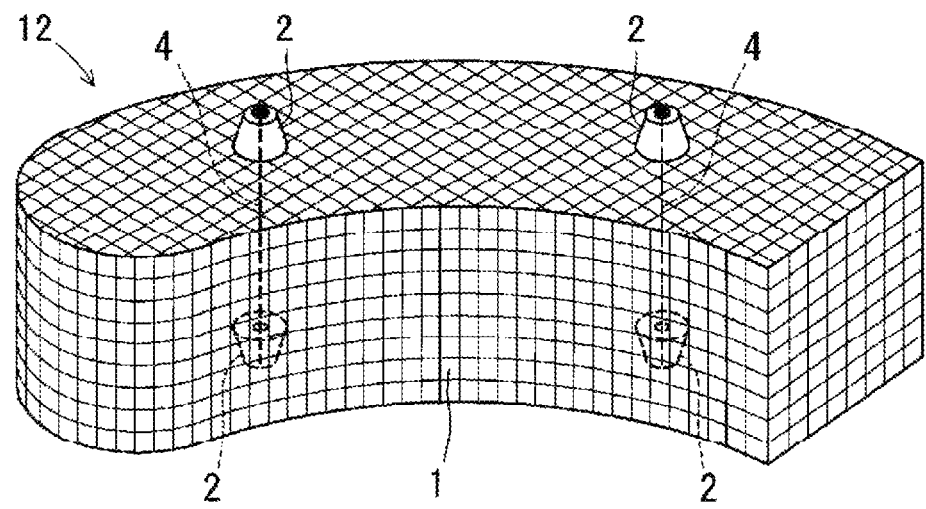
FIG. 7 is a perspective view of the stand-alone type of biomimetic artificial intervertebral disc (comma-shaped bead type for lumbar spine, partial substitution type) relating to another embodiment of the present invention.

The stand-alone type of biomimetic artificial intervertebral disc relating to another embodiment of the present invention is further explained with reference to FIG. 7 and FIG. 8.

This partially-substitution type of artificial intervertebral disc 12 is configured to be arc-state, and one end is formed to be round, and a pair of left and right discs is inserted into a space between vertebral bodies. As the standard size of this artificial intervertebral disc 12, for example, when it is used as the partially-substitution type of artificial intervertebral disc for an adult's lumbar spine, the horizontal width is approximately 9 mm, thickness dimension is approximately 11 mm, a curvature of arc-state center line is approximately 22 mm to 23 mm, and the length dimension along the arc-state center line is approximately 30 mm.

Although this artificial intervertebral disc 12 is different from the totally-substitution type of artificial intervertebral disc 10 in shape, the structure is substantially similar. In other words, two tappets 2 are installed on both the upper and lower surfaces of the structured fabric 1 made of organic fibers where top and bottom flexible surface layer portions are formed, respectively, and the tappets 2 and 2 on both the upper and lower surfaces are connected with the connecting filaments vertically penetrating through the structured fabric 1 under the condition with tension added; concurrently, the bioactive bioceramic powder is sprayed onto both the upper and lower surface layers of the structured fabric 1 or both the upper and lower surface layers of the structured fabric 1 is coated with the complex of the ceramic powder and the biodegradable bioabsorbable polymer, and a bonding property with the vertebral bodies is provided.

Figure 8:
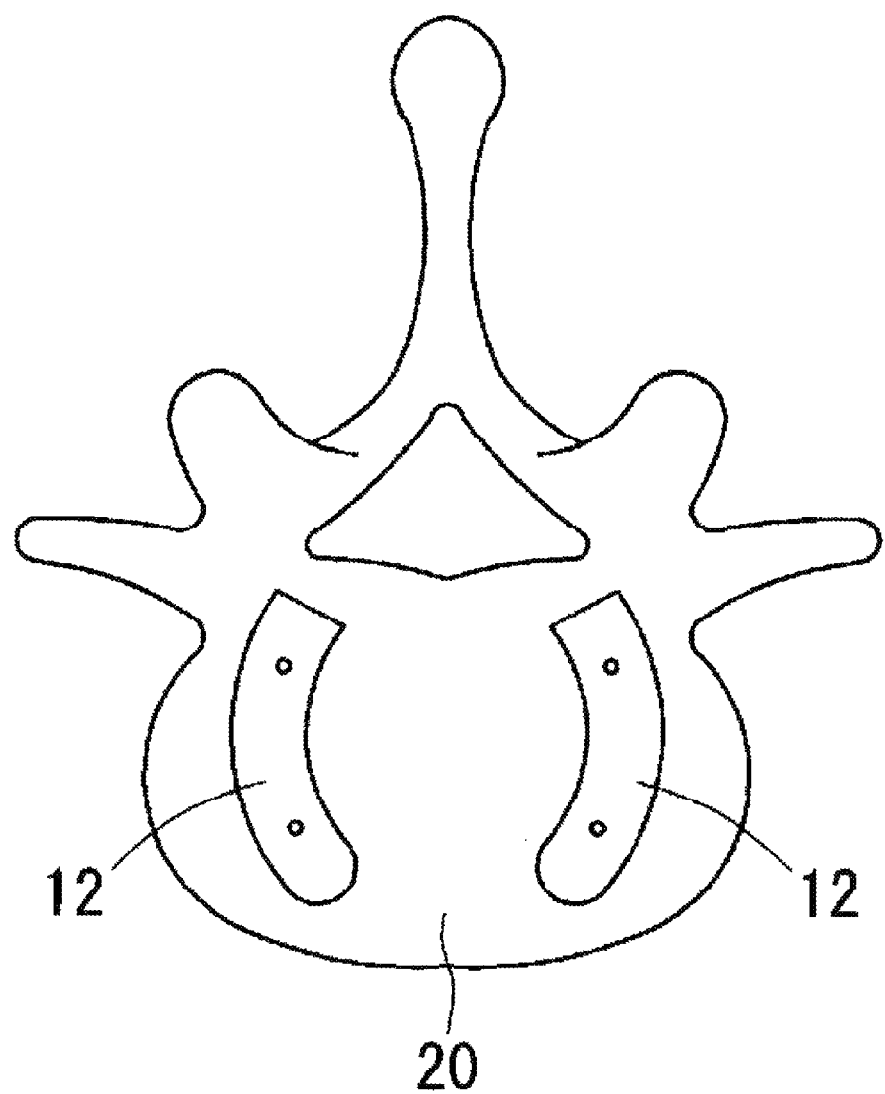
FIG. 8 is a plan view showing an insertion position of the artificial intervertebral disc.

Since such partially-substitution type of artificial intervertebral disc 12 is inserted into the space between the vertebral bodies 20 as a pair of left and right structures from the backside of the vertebral bodies as shown in FIG. 8, the surgery is simpler compared to the totally-substitution type of artificial intervertebral disc 10, and in addition, since the end of the artificial intervertebral disc 12 is formed to be round, the end will never be lodged in the vertebral bodies 20 and it can be smoothly inserted. This insertion fixation can be performed similarly to the operation of spinal fusion cage, which is often clinically used at present. Then, this artificial intervertebral disc 12 also provides a superior function effect similar to the artificial intervertebral disc 10.

Thus, the typical embodiments of the stand-alone type of biomimetic artificial intervertebral disc of the present invention were explained, and the present invention shall not be limited to only these, but there are various modification examples and improved examples using the technical concept of the present invention described in claims, and it is self-evident for persons with ordinary skills in the art pertaining to the present invention to include these examples in the present invention. For example, the number and the shape of the tappet are appropriately modifiable within a scope to obtain the effect of the present invention according to the dimension of the tappet and degree of the roughening.

INDUSTRIAL APPLICABILITY

The stand-alone type of biomimetic artificial intervertebral disc of the present invention can be easily inserted into the intervertebral space by satisfying minimally invasive conditions to reduce the intervertebral expansion as much as possible and not to damage the vertebral bodies as much as possible, and the tappets mounted on both the upper and lower surfaces of the structured fabric are fitted into the holes formed in the endplate surface of the upper and lower vertebral bodies, and the structured fabric is certainly fixed in the stand-alone manner so as not cause any dislodging or position gap, and it is highly reliable that the biomimetic structured fabric follows the movement of the vertebral bodies and is biomimetically deformed and plays a role as an intervertebral disc throughout a long term, and it is clinically truly effective that the fitting state of the tappets, the contact state and binding state with the vertebral body surfaces can be observed.

DESCRIPTION OF SYMBOLS 1 structured fabric
1a inner layer portion of structured fabric
1b top and bottom surface layer portions of structured fabric
2 tappet
2a through-hole of tappet
2b abutting surface with structured fabric of tappet
4 connecting filament
5 layer sprayed with bioactive bioceramic powder or layer coated with complex of powder and biodegradable, bioabsorbable polymer
10, 11, 12 artificial intervertebral disc
20 vertebral body
20a hole formed in endplate surface of vertebral body

What is claimed is:

1. A stand-alone type of biomimetic artificial intervertebral disc, comprising:
   a structured fabric comprising organic fibers; and
   tappets mounted on an upper surface and a lower surface of the structured fabric,
   wherein the organic fibers form a three-dimensional fabric,
   wherein the organic fibers are disposed on at least three axes, or the organic fibers are interwoven, or the organic fibers are disposed on at least three axes and at least some of the organic fibers are interwoven,
   wherein an entirety of positions between the upper surface and the lower surface of the structured fabric comprise the organic fibers,
   wherein the tappet mounted on the upper surface of the structured fabric and the tappet mounted on the lower surface are connected with a connecting filament penetrating through the structured fabric vertically under tension, the connecting filament having been inserted while the structured fabric is compressed, and
   wherein a distance between the tappet mounted on the upper surface of the structured fabric and the tappet mounted on the lower surface is slightly shorter than a distance between the upper surface and the lower surface of the structured fabric.

2. The stand-alone type of biomimetic artificial intervertebral disc according to claim 1, wherein the tappet height is 1.0 mm to 3.0 mm, and
   wherein an abutting surface of the tappet with the structured fabric is a flat surface, a convex curve that convexly curves to the structured fabric side, or a concave curve that concavely curves to the structured fabric side.

3. The stand-alone type of biomimetic artificial intervertebral disc according to claim 1, wherein the tappet height is 0.3 mm to 1.0 mm, and at least five tappets are mounted on the upper surface and the lower surface of the structured fabric, respectively.

4. The stand-alone type of biomimetic artificial intervertebral disc according to any of claims 1 to 3, wherein the tappet comprises radiopaque bioceramics.

5. The stand-alone type of biomimetic artificial intervertebral disc according to any of claims 1 to 3, wherein the tappet comprises radiopaque and bioactive bioceramics.

6. The stand-alone type of biomimetic artificial intervertebral disc according to any of claims 1 to 3, wherein the tappet comprises a complex comprising powder of radiopaque and bioactive bioabsorbable bioceramics and a biodegradable, bioabsorbable polymer.

7. The stand-alone type of biomimetic artificial intervertebral disc according to any of claims 1 to 3, wherein an upper surface layer portion and a lower surface layer portion of the structured fabric are more flexible than other portions of the structured fabric.

8. The stand-alone type of biomimetic artificial intervertebral disc according to claim 7, wherein bioactive bioceramics powder is sprayed onto the upper surface layer portion and the lower surface layer portion of the structured fabric.

9. The stand-alone type of biomimetic artificial intervertebral disc according to claim 7, wherein the upper surface layer portion and the lower surface layer portion of the structured fabric are coated with a complex of bioactive bioceramics powder and a biodegradable, bioabsorbable polymer.

10. The stand-alone type of biomimetic artificial intervertebral disc according to claim 1, wherein the tappets are shaped as beheading cone, sphere, semi-sphere, spindle, beheading pyramid, cylinder, or square column.

11. The stand-alone type of biomimetic artificial intervertebral disc according to claim 1, wherein the connecting filament penetrating through the structured fabric is substantially perpendicular to the upper surface and the lower surface of the structured fabric at positions where the tappets are mounted.

* * * * *